United States Patent [19]

Igarashi et al.

[11] 4,113,870
[45] Sep. 12, 1978

[54] METHOD FOR TREATMENT OF HYPERTENSION

[75] Inventors: Toshiji Igarashi, Tokorozawa; Yoshikage Nakajima, Tokyo, both of Japan

[73] Assignee: Eisai Co., Ltd., Tokyo, Japan

[21] Appl. No.: 821,910

[22] Filed: Aug. 4, 1977

[30] Foreign Application Priority Data

Aug. 11, 1976 [JP] Japan .................................. 51-94948

[51] Int. Cl.² ......................................... A61K 31/455
[52] U.S. Cl. ................................................. 424/266
[58] Field of Search ........................................ 424/266

[56] References Cited
U.S. PATENT DOCUMENTS 3,890,333  6/1975  Nakamura et al. .................. 424/266

*Primary Examiner*—Donald B. Moyer
*Attorney, Agent, or Firm*—Blanchard, Flynn, Thiel, Boutell & Tanis

[57] ABSTRACT

Hypertension can be treated with a nicotinate of chroman of the formula:

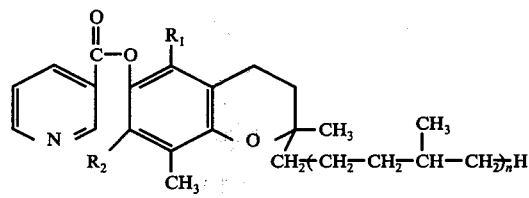

wherein $n$ is an integer of from 0 to 3, $R_1$ stands for

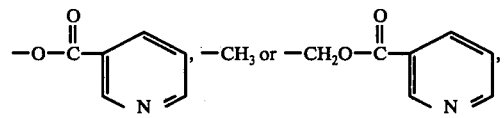

and $R_2$ stands for —$CH_3$ or

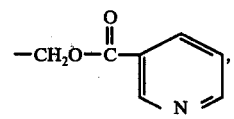

with the proviso that when $R_1$ is

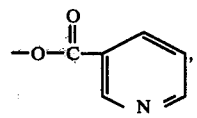

$R_2$ is —$CH_3$ and the case where both of $R_1$ and $R_2$ stand for —$CH_3$ is excluded.

8 Claims, No Drawings

METHOD FOR TREATMENT OF HYPERTENSION

BACKGROUND OF THE INVENTION

1. Field of Invention

The present invention relates to a method of treating hypertension which comprises administering nicotinate of a chroman compound represented by the following general formula (I):

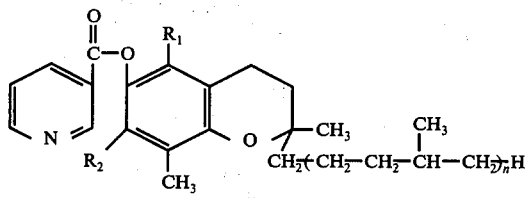

wherein $n$ is an integer of from 0 to 3, $R_1$ stands for a group

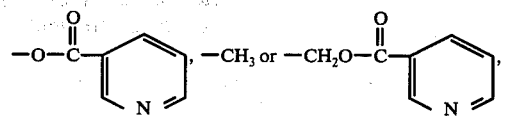

and $R_2$ stands for a group —$CH_3$ or

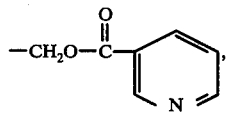

with the proviso that when $R_1$ is a group

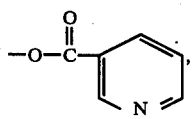

$R_2$ is a group —$CH_3$ and the case where both of $R_1$ and $R_2$ stand for a group —$CH_3$ is excluded.

2. Description of Prior Arts

Various antihypertensive agents have heretofore been used for treatment of hypertension. However, these agents have various harmful side effects and administration of these agents, especially administration of large amounts or long-time continuous administration, involves various problems. For example, diuretic antihypertensive agents represented by sulfonamide and thiazide compounds cause serious side effects such as uricacidedemia and hypokalemia, and sympatholytic agents such as reserpine and Methyl-DOPA preparation cause side effects such as thirst, clouding of consciousness and orthostatic hypotensive asthenia. Further, vasodilators such as Apresoline (trademark) often cause headache, tachycardia, angina pectoris and other side effects.

SUMMARY OF INVENTION

As a result of our research works with a view to developing a new antihypertensive agent having a safer blood pressure-reducing activity and which is free of the foregoing side effects, we have found that compounds of the present invention represented by the above general formula (I) have a safer antihypertensive activity with none of the above-mentioned side effects. Therefore, it is a primary object of the present invention to provide a method for treatment of hypertension. It is another object of the present invention to provide a medicine for treatment of hypertension. Still another object of the present invention is to provide a hypertensive agent which produces such reduced side effects and can be administered continuously for a long time.

Results of animal tests made on the pharmacological actions and toxicities (acute toxicities) of the compounds of the present invention will now be described.

Pharmacological Tests

The hypotensive effect of the compounds of this invention was determined in spontaneous hypertension rats (hereinafter referred to as "SHR," purchased from Nippon Rat K.K.)

Method

The hypotensive effect of test compounds on SHR were measured, using SHR's of chronic hypertension which were 48 weeks old as test animals. The maximum blood pressure was about 250 mm Hg.

The test compound was orally administered to SHR in the form of a suspension in gum arabic. SHR's were divided into groups according to the amount administered of the test compound, each group consisting of 6 SHR's. Further, a control group of 6 SHR's, to which no compound was administered, was similarly tested.

The blood pressure was measured by a Shimazu type continuous blood pressure measuring apparatus (Model SCS-301 manufactured by Shimazu Seisakusho K.K., Japan). The systolic blood pressure was measured on the tail artery. The measurement was performed at times of 3 hours, 6 hours, 9 hours and 24 hours after administration of the test compound, and the change of the blood pressure with the passing of time was examined.

Test Compounds and Doses

5-Nicotinoyloxymethyl-γ-tocopheryl nicotinate (hereinafter referred to as "compound A"): 0.4 mg/Kg, 2 mg/Kg, 10 mg/Kg and 50 mg/Kg α-Tocopheryl nicotinate (hereinafter referred to as "compound B"): 10 mg/Kg

Results

The changes of the blood pressure in SHR's by administration of the test compounds are summarized in Table 1.

Table 1

| | | Hypotensive Effect of Test Compounds on SHR's Blood Pressure | | | | |
|---|---|---|---|---|---|---|
| Test Compound | Doses (mg/Kg) | (mmHg) at Start of Test | Change of Blood Pressure (mmHg) after Administration | | | |
| | | | 3 hours | 6 hours | 9 hours | 24 hours |
| Compound A | 0.4 | 253±4.8 | 243±6.6 | 238±7.0 | 243±5.9 | 247±4.8 |
| | 2 | 252±3.6 | *224±5.4 | *221±5.4 | 228±2.8 | 244±2.7 |
| | 10 | 258±4.0 | *231±6.6 | *225±5.3 | *226±2.4 | 254±4.4 |
| | 50 | 255±2.2 | *221±4.0 | *221±3.8 | *218±4.6 | *238±3.1 |

Table 1-continued

| Test Compound | Doses (mg/Kg) | Hypotensive Effect of Test Compounds on SHR's Blood Pressure (mmHg) at Start of Test | Change of Blood Pressure (mmHg) after Administration | | | |
|---|---|---|---|---|---|---|
| | | | 3 hours | 6 hours | 9 hours | 24 hours |
| Compound B | 10 | 253±3.6 | 250±5.6 | 246±5.1 | 240±3.2 | 252±3.1 |
| Control | — | 248±3.8 | 243±3.1 | 243±3.8 | 243±3.3 | 251±4.4 |

*verification of the difference of reduction of the blood pressure between compounds A and B (significant difference was observed with a significance level P of 0.01)

As will be apparent from the results shown in Table 1, the compound A manifested a hypotensive effect at a dose of 0.4 mg/Kg, and the blood pressure of 253 mm Hg before administration was reduced to 243 mm Hg after 3 hours from administration and to 238 mm Hg after 6 hours from administration. When the dose was 2 mg/Kg, the blood pressure of 252 mm Hg before administration was reduced to 224 mm Hg after 3 hours from administration and to 221 mm Hg after 6 hours from administration. When the dose was 10 mg/Kg, the blood pressure of 258 mm Hg before administration was reduced to 231 mm Hg after 3 hours from administration and to 225 mm Hg after 6 hours from administration and this low blood pressure was maintained even after 9 hours from administration.

When the compound B was administered in a dose of 10 mg/Kg, the blood pressure of 253 mm Hg before administration was charged to 250 mm Hg after 3 hours from administration and to 240 mm Hg after 6 hours from administration. This change of the value of the blood pressure is not statistically significant. In other words, the compound B did not manifest a hypotensive effect in the acute test where the compound was administered only once.

Acute Toxicity Tests

Male mice of the dd strain were used as test animals, and test compounds were orally administered in the form of a suspension in gum arabic.

In each of the compounds A and B, no particular toxication was observed at an administered amount of 1 g/Kg and no test animal was killed.

As will be apparent from the foregoing results of the pharmacological and toxicity tests, the compounds of the general formula (I) of the present invention represented by the compound A have an excellent antihypertensive activity and are very safe because no substantial toxicity is observed. Accordingly, it is expected that the compounds of the present invention are very effective for treatment and prevention of renal hypertension, cardiac hypertension, endocrine hypertension, nervous hypertension and essential hypertension and the like. The fact that the compounds of the present invention manifested a antihypertensive effect at tests using sponteneous hypertension rats is very significant. As a result of examination of reactions of various antihypertensive agents to spontaneous rats and as a result of etiological research works made on these spontaneous hypertension rats, it has been confirmed that this disease animal is suitable as a model of essential hypertension. Therefore, it is construed that the compounds of the general formula (I) of the present invention will be very effective for treatment of essential hypertension.

The amounts of the compounds of the general formula (I) of the present invention to be administered and the administration methods are appropriately chosen and adjusted depending on the conditions of diseases to be medically treated. In general, in the case of oral administration to adults, the compounds of the general formula (I) are employed in an amount of 10 to 2500 mg, preferably 20 to 200 mg, per day.

The compounds of the general formula (I) may be formed in pharmaceutical preparations according to customary techniques.

Accordingly, the present invention includes a pharmaceutical composition suitable as a medicine to be administered to men, which comprises at least one of the compounds represented by the above-mentioned general formula (I). This composition is prepared by using an optional pharmaceutical carrier or excipient and is administered according to a conventional method.

It is preferred that the pharmaceutical composition be administered in a form suitable for absorption from the stomach and intestinal tracts. As the oral administration form including a unit dose, there can be mentioned tablets and capsules. These tablets and capsules may comprise binders such as syrup, tragacanth gum, gum arabic, gelatin, sorbitol and polyvinyl pyrrolidone, excipients such as lactose, sugar, corn starch, microcrystalline cellulose, calcium phosphate, sorbitol and glycine, lubricants such as magnesium stearate, talc, polyethylene glycol and silica, disintegrator such as potato starch and calcium carboxymethylcellulose, and pharmaceutically acceptable wetting agents such as sodium lauryl sulfate. Tablets may be coated according to methods known in the art. Liquid preparations for oral administration may be aqueous and oily suspensions, solutions, syrups, elixirs and the like. They may be dry products which are re-dissolved in water or other suitable vehicles before administration. These liquid preparations may comprise additives customarily used in this field, for example, suspending agents such as sorbitol syrups, methylcellulose, glucose/sugar syrups, gelatin, hydroxyethylcellulose, carboxymethylcellulose, aluminum stearate gels and hydrogenated edible fats, emulsifiers such as lecithin, sorbitan mono-oleate and gum arabic, non-aqueous vehicles such as almond oil, sesame oil, fractionated coconut oil, octyldecyl triglyceride, propylene glycol and ethyl alcohol, and antiseptics such as methyl p-hydroxybenzoate, propyl p-hydroxybenzoate and sorbic acid.

An injection composition is provided in the form of an ampoule containing a unit administration amount or in the state filled in a multi-administration unit amount vessel together with an antiseptic additive. The composition may be a suspension, a solution or an emulsion in an oily or aqueous vehicle, and it may further comprise a suspending agent, a stabilizer and/or a dispersing agent. Moreover, the active ingredient may be in the form of a powder which is dissolved in a suitable vehicle such as sterilized water free of a pyrogenic substance before administration.

The present invention will now be described by reference to the following Examples.

EXAMPLE 1 (Capsule)

| | |
|---|---|
| 5-Nicotinoyloxymethyl-γ-tocopheryl nicotinate | 5 g |
| Microcrystalline cellulose | 80 g |
| Corn starch | 22 g |
| Polyvinyl pyrrolidone | 3 g |
| Total | 130 g |

The above components were granulated according to a customary method, and the resulting granule was filled in 1000 gelatin hard capsules. Each capsule contains 5 mg of 5-nicotinoyloxymethyl-γ-tocopheryl nicotinate.

EXAMPLE 2 (Powder)

| | |
|---|---|
| 5-Nicotinoyloxymethyl-γ-tocopheryl nicotinate | 50 g |
| Microcrystalline cellulose | 400 g |
| Corn starch | 550 g |
| Total | 1000 g |

5-Nicotinoyloxymethyl-γ-tocopheryl nicotinate was dissolved in acetone and the solution was adsorbed on microcrystalline cellulose. The cellulose was then dried and mixed with corn starch, and the mixture was formed into a powder according to a customary method 20 trituration of 5-nicotinoyloxymethyl-γ-tocopheryl nicotinate was then prepared.

EXAMPLE 3 (Tablet)

| | |
|---|---|
| 5-Nicotinoyloxymethyl-γ-tocopheryl nicotinate | 5 g |
| Corn starch | 10 g |
| Refined sugar | 20 g |
| Calcium carboxymethylcellulose | 10 g |
| Microcrystalline cellulose | 40 g |
| Polyvinyl pyrrolidone | 5 g |
| Talc | 10 g |
| Total | 100 g |

5-Nicotinoyloxymethyl-γ-tocopheryl nicotinate was dissolved in acetone and adsorbed on microcrystalline cellulose. The cellulose was dried and mixed with corn starch, refined sugar and calcium carboxymethylcellulose, and the mixture was granulated according to a customary method using an aqueous solution of polyvinyl pyrrolidone as a binder. The resulting granule was mixed with talc as a lubricant and formed into tablets, each having a weight of 100 mg and containing 5 mg of 5-nicotinoyloxymethyl-γ-tocopheryl nicotinate.

EXAMPLE 4 (Injection)

| | |
|---|---|
| Nicotinoyloxymethyl-γ-tocopheryl nicotinate | 10 g |
| Nikkol HCO-60 (registered trademark for product of Nikko Chemical Company) | 40 g |
| Sesame oil | 2 g |
| Sodium chloride | 9 g |
| Propylene glycol | 50 g |
| Distilled water | balance |
| Total | 1000 ml |

A mixture of 5-nicotinoyloxymethyl-γ-tocopheryl nicotinate, Nikkol HCO-60, sesame oil and propylene glycol was heated at about 80° C. and was mixed with distilled water in which sodium chloride had been dissolved in advance and which was heated at about 80° C. to form 1000 ml of an aqueous solution. The aqueous solution was sterilely filtered and filled in brown ampoules having a capacity of 1 ml. The ampoules were melt-sealed and sterilized under heating. Each ampoule contained 40 mg of 5-nicotinoyloxymethyl-γ-tocopheryl nicotinate.

EXAMPLE 5 (Granule)

| | |
|---|---|
| 5-Nicotinoyloxymethyl-γ-tocopheryl nicotinate | 10 g |
| Silicic anhydride | 30 g |
| Crystalline cellulose | 5 g |
| Mannitol | 49 g |
| Polyvinyl pyrrolidone | 6 g |
| Total | 100 g |

Granules were prepared from the above components according to a customary method.

EXAMPLE 6 (Soft Capsule)

| | |
|---|---|
| 5-Nicotinoyloxymethyl-γtocopheryl nicotinate | 5 g |
| Octyldecyl triglyceride | 20 g |
| Sesame oil | 4 g |
| Total | 29 g |

From the foregoing components were prepared 100 soft capsules according to the customary method.

Each soft capsule contained 50 mg of 5-nicotinoyloxymethyl-γ-tocopheryl nicotinate.

What is claimed is:

1. A method of treating hypertension which comprises administering to a hypertensive subject requiring such treatment, a therapeutically effective amount of a compound having the formula:

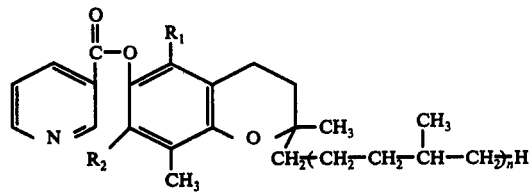

wherein $n$ is an integer of from 0 to 3, $R_1$ is

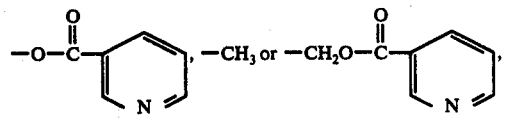

and $R_2$ is —$CH_3$ or

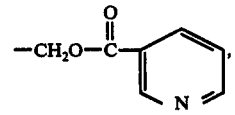

with the proviso that when $R_1$ is

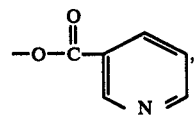

$R_2$ is —$CH_3$ and with the further proviso that $R_1$ and $R_2$ are not —$CH_3$ simultaneously.

2. A method according to claim 1 in which said compound is 7-nicotinoyloxymethyl-β-tocopheryl nicotinate.

3. A method according to claim 1 in which said compound is 5-nicotinoyloxymethyl-γ-tocopheryl nicotinate.

4. A method according to claim 1 in which said compound is 5,7-bis-nicotinoyloxymethyl-δ-tocopheryl nicotinate.

5. A method according to claim 1 in which said compound is 5-nicotinoyloxy-γ-tocopheryl nicotinate.

6. A method according to claim 1 in which said hypertension is essential hypertension.

7. A method according to claim 1 in which said therapeutically effective amount is a daily dose of 10–2500 mg of said compound administered orally.

8. A method according to claim 1 in which said therapeutically effective amount is a daily dose of 10–2500 mg of said compound administered by injection.

* * * * *